US010737067B2

(12) United States Patent
Kobayashi et al.

(10) Patent No.: US 10,737,067 B2
(45) Date of Patent: Aug. 11, 2020

(54) GUIDING CATHETER FOR RENAL ARTERY AND METHOD FOR USING THE SAME

(71) Applicant: TERUMO KABUSHIKI KAISHA, Shibuya-ku, Tokyo (JP)

(72) Inventors: Junichi Kobayashi, Cupertino, CA (US); Wataru Karino, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 462 days.

(21) Appl. No.: 15/001,821

(22) Filed: Jan. 20, 2016

(65) Prior Publication Data

US 2016/0136394 A1    May 19, 2016

Related U.S. Application Data

(63) Continuation of application No. PCT/JP2014/069647, filed on Jul. 25, 2014.

(30) Foreign Application Priority Data

Aug. 1, 2013    (JP) .................................. 2013-160774

(51) Int. Cl.
*A61M 25/01*    (2006.01)
*A61M 25/00*    (2006.01)
*A61M 25/09*    (2006.01)

(52) U.S. Cl.
CPC .... *A61M 25/0152* (2013.01); *A61M 25/0043* (2013.01); *A61M 25/0138* (2013.01);
(Continued)

(58) Field of Classification Search
CPC .......... A61M 25/0152; A61M 25/0147; A61M 25/0043; A61M 25/0138; A61M 2025/0161
See application file for complete search history.

(56) References Cited

U.S. PATENT DOCUMENTS

| 5,439,006 A | 8/1995 | Brennen et al. |
| 5,876,385 A * | 3/1999 | Ikari ................. A61M 25/0041 604/523 |

(Continued)

FOREIGN PATENT DOCUMENTS

| JP | 8-112245 A | 5/1996 |
| JP | 8-510666 A | 8/2007 |

(Continued)

OTHER PUBLICATIONS

Written Opinion (PCT/ISA/237) dated Oct. 21, 2014, by the Japanese Patent Office as the International Searching Authority for International Application No. PCT/JP2014/069647.

(Continued)

*Primary Examiner* — Lauren P Farrar
*Assistant Examiner* — James D Ponton
(74) *Attorney, Agent, or Firm* — Buchanan Ingersoll & Rooney PC

(57) ABSTRACT

A catheter body of a guiding catheter configured to be introduced into the renal artery, the catheter body including a plurality of abutting portions abutting at least two sites of the inner wall of the aorta on the abdominal side relative to the heart when the distal portion is disposed in the renal artery. A method for using a guiding catheter for the renal artery including providing the guiding catheter for the renal artery; inserting the guiding catheter from an artery in the arm and disposing a distal portion of the guiding catheter in the renal artery via the aorta; and causing the plurality of abutting portions to abut the inner wall of sections further on the abdominal side than the heart, in the aorta.

3 Claims, 9 Drawing Sheets

(52) U.S. Cl.
CPC ........ *A61M 25/0147* (2013.01); *A61M 25/09* (2013.01); *A61M 2025/0161* (2013.01); *A61M 2210/127* (2013.01)

(56) References Cited

U.S. PATENT DOCUMENTS

| | | | |
|---|---|---|---|
| 5,885,247 A * | 3/1999 | Slagboom | A61M 25/0041 604/200 |
| 7,585,836 B2 * | 9/2009 | Goodson, IV | A61K 38/2242 514/1.1 |
| 2002/0115982 A1 * | 8/2002 | Barbut | A61B 5/0215 604/509 |
| 2006/0036218 A1 * | 2/2006 | Goodson, IV | A61M 25/0054 604/264 |
| 2007/0208302 A1 | 9/2007 | Webster et al. | |
| 2008/0300573 A1 * | 12/2008 | Consigny | A61L 27/54 604/509 |
| 2011/0071503 A1 | 3/2011 | Takagi et al. | |
| 2014/0018732 A1 * | 1/2014 | Bagaoisan | A61M 25/0136 604/95.04 |
| 2014/0275993 A1 * | 9/2014 | Ballakur | A61N 5/00 600/424 |

FOREIGN PATENT DOCUMENTS

| | | |
|---|---|---|
| JP | 2009-524490 A | 7/2009 |
| JP | 2009-273640 A | 11/2009 |
| JP | 2011-083596 A | 4/2011 |
| JP | 2012-513873 A | 6/2012 |
| WO | WO 94/27666 A1 | 12/1994 |
| WO | WO 2007/089570 A2 | 8/2007 |
| WO | WO 2010/078175 A1 | 7/2010 |

OTHER PUBLICATIONS

English translation of the International Search Report (PCT/ISA/210) dated Oct. 21, 2014, by the Japanese Patent Office as the International Searching Authority for International Application No. PCT/JP2014/069647.

* cited by examiner

GUIDING CATHETER FOR RENAL ARTERY AND METHOD FOR USING THE SAME

CROSS-REFERENCES TO RELATED APPLICATIONS

This application is a continuation of International Application No. PCT/JP2014/069647 filed on Jul. 25, 2014, and claims priority to Japanese Application No. 2013-160774 filed on Aug. 1, 2013, the entire content of both of which is incorporated herein by reference.

TECHNICAL FIELD

This application relates to a guiding catheter for insertion into a renal artery. The guiding catheter is inserted into a blood vessel from an artery in the arm and a distal portion of the guiding catheter is introduced into the renal artery via the aorta. This application also relates to a method for using the guiding catheter.

BACKGROUND DISCUSSION

Some patients possess intractable high blood pressure such that it is difficult to improve the condition of high blood pressure even by taking a hypotensive drug. Reduction in blood pressure can be expected by cutting or damaging sympathetic nerves around the renal artery and by blocking the transmission of the sympathetic nerves.

A manual operation performed using an ablation device can percutaneously cut the sympathetic nerves of the renal artery. One method of using an ablation device possessing an electrode portion at the distal end of an elongated shaft, includes bringing the electrode portion into contact with an inner wall of the renal artery, and applying heat energy to the sympathetic nerves around the renal artery to cauterize the sympathetic nerves (for example, refer to JP-T-2012-513873).

When performing treatment on the renal artery using the ablation device, a guiding catheter is required to assist smooth insertion of the ablation device and to apply sufficient back-up force to safely and efficiently lead the ablation device to the target renal artery. Note that although not related to guiding an ablation device, examples of guiding a catheter in related art are found in the disclosures of JP-A-2009-273640 and JP-A-2011-83596.

In conventional manual operation in which treatment is performed on the renal artery using an ablation device, an ablation device is generally inserted into a guiding catheter after the guiding catheter has been inserted into the renal artery from the artery of the femur close to the renal artery and a distal portion of the guiding catheter has moved to within the target renal artery.

SUMMARY

About 90% of human renal arteries are branched downward (i.e., towards the individual's feet when standing) or in a right-angled direction from the aorta. When introducing a guiding catheter from the artery of the femur, it is necessary to change the direction of the distal portion of the guiding catheter to an opposite direction from the traveling direction in the aorta in order to insert the distal portion of the guiding catheter into the downward renal artery. In contrast, the introduction of the guiding catheter from an artery in the arm (for example, from the radial artery or the brachial artery) has an easier approach to the downward renal artery than the approach from the femoral artery.

When introducing a guiding catheter from the artery of the femur, it is necessary to have complete rest in a supine position (i.e., the patient must lie down on their back) to stop bleeding of a puncture site after the surgery. Maintaining this position for a length of time can burden the patient. In contrast, when introducing a guiding catheter from an artery in the arm, the patient can walk immediately after surgery. There is thus a benefit in introducing the guiding catheter from an artery in the arm because the operation is less burdensome on the patient.

However, when introducing a guiding catheter from an artery in the arm, the guiding catheter, and an ablation device which has been inserted into the guiding catheter, tremble due to the influence of the pulsation of the heart or a pulsatile flow of blood within a section between the thoracic aorta and the abdominal aorta. As a result, a vibration is transmitted to the electrode portion at the distal end of the ablation device and the impedance during the application of energy is not stabilized. There is thus a concern that it may become difficult to perform the manual operation. In addition, if the electrode portion vibrates, heat energy is applied to a wider range than intended and the damaged range may be overly wide. If the electrode portion further vibrates, the heat energy applied to the inner surface of a blood vessel per unit area may decrease, and thus, the intended ablation effect cannot be obtained.

The guiding catheter and method of using the guiding catheter disclosed in this application addresses the problems discussed above. The guiding catheter for the renal artery and the method of using the guiding catheter can suppress a vibration caused by the pulsation of the heart or a pulsatile flow of blood.

The guiding catheter here is configured to be inserted into a blood vessel from an artery in an arm of a living body. The guiding catheter includes a flexible catheter body possessing a distal portion configured to be introduced into a renal artery of the living body by way of an aorta, which is connected to a heart of the living body, after inserting the guiding catheter into the blood vessel. The catheter body includes a plurality of abutting portions that abut at least two sites of an inner wall of the aorta when the distal portion of the catheter body is disposed in the renal artery, the two different sites of the inner wall of the aorta being on an abdominal side below the heart.

According to the aforesaid configuration, since the plurality of abutting portions of the catheter body abut on at least two sites of the inner wall of the aorta further on the abdominal side than the heart, it is possible to suppress the vibration of the catheter body caused by the influence of the pulsation of the heart or a pulsatile flow of blood. Accordingly, it is possible to suppress and stabilize the vibration of the electrode portion when performing ablation treatment on biological tissue using the electrode portion at the distal end by inserting the ablation device into the guiding catheter.

In the aforesaid guiding catheter for the renal artery, the plurality of abutting portions may abut on the inner wall of the abdominal aorta. According to this configuration, since the plurality of abutting portions abut sites of the inner wall of the aorta away from the heart, the pulsation of the heart is hardly transmitted to the catheter body, and therefore, it is possible to further suppress the vibration of the catheter body.

In the aforesaid guiding catheter for the renal artery, the plurality of abutting portions may include a first curve possessing a distal end and a second curve possessing a proximal end, and the catheter body may further include an intermediate portion connected to the distal end of the first curve and the proximal end of the second curve. According to this configuration, the catheter body is stably supported by the first curve and the second curve abutting the inner wall of the aorta. Accordingly, it is possible to effectively suppress the vibration of the catheter body.

In the aforesaid guiding catheter for the renal artery, the first curve may possess a first curvature and the second curve may possess a second curvature, the first curvature being in a direction opposite to the direction of the second curvature. According to this configuration, since the first curve and the second curve abut the inner wall of the aorta at sites opposite to each other, the catheter body is stably fixed to the aorta. Accordingly, it is possible to effectively suppress the vibration of the catheter body.

In the aforesaid guiding catheter for the renal artery, the first curve, the intermediate portion, and the second curve may form a shaped portion of the catheter body, a first length of the shaped portion being longer than an inner diameter of the aorta when the shaped portion is positioned in the aorta and the distal portion of the catheter body is disposed in the renal artery, the first length being measured in a direction orthogonal to a longitudinal direction of the guiding catheter. According to this configuration, it is possible to make the first curve and the second curve reliably abut the inner wall of the aorta at sites opposite to each other, and therefore, the catheter body is stably fixed to the aorta.

In the aforesaid guiding catheter for the renal artery, a second length of the shaped portion may be shorter than the first length of the shaped portion, the second length being measured in the longitudinal direction of the guiding catheter. According to this configuration, with the second length of the shaped portion being appropriately short, when the distal portion of the catheter body is disposed in the renal artery, it is possible to easily dispose the first curve which is positioned further on the proximal side, out of the first curve and the second curve, at a position away from the heart. Accordingly, it is possible to effectively suppress the vibration of the catheter body.

In the aforesaid guiding catheter for the renal artery, the catheter body may have a first extension portion extending from the first curve in a proximal direction, and a second extension portion extending from the second curve in a distal direction, with the second extension portion connected to the distal portion. An extension line extending proximally from the second extension portion may intersect the first extension portion. According to this configuration, it is possible to make the length of the second curve coming into contact with an inner wall of the aorta appropriately short, and therefore, it is possible to reduce the burden on the inner wall of the aorta.

In the aforesaid guiding catheter for the renal artery, the catheter body may have an extension portion connected to the second curve and the distal portion. The length of the extension portion may be longer than the length of the renal artery. According to this configuration, even when the distal portion of the catheter body is put into a back side of the renal artery, it is possible to favorably maintain the state in which the first curve and the second curve abut the inner wall of the aorta without the second curve (curve on the distal side) entering the renal artery.

The aforesaid guiding catheter for the renal artery may further include a shape control mechanism configured to move the first curve and the second curve to enter a desired curved state. According to this configuration, it is possible to make the first curve and the second curve enter a desired curved state through the action of the shape control mechanism even in a state in which the ablation device is inserted into the catheter body. Accordingly, it is possible to make the first curve and the second curve reliably abut the inner wall of the aorta.

In the aforesaid guiding catheter for the renal artery, the shape control mechanism may include a traction wire possessing a distal end, the distal end of the traction wire being fixed to the catheter body at a position distal of the second curve, the traction wire extending along the catheter body proximally of the first curve. The traction wire may be configured to be pulled in the proximal direction with respect to the catheter body to increase the first curvature of the first curve and the second curvature of the second curve in accordance with movement of the traction wire in the proximal direction with respect to the catheter body. According to this configuration, it is possible to control the curved states of the first curve and the second curve with the simple structure using the traction wire.

In the aforesaid guiding catheter for the renal artery, a guide portion may be in the intermediate portion, a part of the traction wire being slidably positioned in the guide portion. According to this configuration, it is possible to smoothly and reliably control the curved states of the first curve and the second curve.

In the aforesaid guiding catheter for the renal artery, the first curve may include a plurality of first joint members connected to each other in an axial direction. The second curve may include a plurality of second joint members connected to each other in the axial direction. The shape control mechanism may include a first traction wire extending along the catheter body and being operable to change a shape of the first curve, and a second traction wire extending along the catheter body and being operable to change a shape of the second curve. When the first traction wire is pulled in a proximal direction, the first curvature of the first curve may increase in accordance with the movement of the first traction wire in the proximal direction of the catheter body. When the second traction wire is pulled in the proximal direction, the second curvature of the second curve may increase in accordance with the movement of the second traction wire in the proximal direction of the catheter body. According to this configuration, it is possible to individually control the curved state of each of the first curve and the second curve using the two traction wires.

In addition, according to the present invention, there is provided a method for inserting a guiding catheter into a renal artery of a living body, the method including inserting the guiding catheter into a blood vessel of the living body by way of an artery in an arm of the living body, the guiding catheter possessing a distal portion, the living body having an aorta connected to a heart and a renal artery; moving the guiding catheter into and along the aorta, and disposing the distal portion of the guiding catheter in the renal artery via the aorta; and causing a plurality of abutting portions of the guiding catheter to abut two spaced apart sites of the inner wall of the aorta, the two spaced apart sites of the inner wall of the aorta being on an abdominal side below the heart in the aorta.

According to the aforesaid method, since the plurality of abutting portions of the catheter body abut on at least two sites on the inner wall of the aorta further on the abdominal side than the heart, it is possible to suppress the vibration of the catheter body caused by the influence of the pulsation of the heart or a pulsatile flow of blood. Accordingly, it is possible to suppress and stabilize the vibration of the electrode portion when performing ablation treatment on biological tissue using the electrode portion at the distal end by inserting the ablation device into the guiding catheter.

In the aforesaid method for using a guiding catheter, the aorta may be an abdominal aorta, and the two spaced apart sites are two spaced apart sites on the inner wall of the abdominal aorta. Accordingly, the plurality of abutting portions abut on sites away from the heart. Thus, the pulsation of the heart is hardly transmitted to the catheter body, and therefore, it is possible to further suppress the vibration of the catheter body.

In the aforesaid method for using a guiding catheter, the plurality of abutting portions may include a first curve and a second curve, a part of the first curve and a part of the second curve may abut the two sites on the inner wall of the aorta on diametrically opposite sides of the aorta. Accordingly, it is possible to effectively suppress the vibration of the catheter body.

In the aforesaid method for using a guiding catheter, the guiding catheter may include a lumen, and the moving of the guiding catheter along the aorta may be performed while a guide wire is located in the lumen of the guiding catheter. The method for using the guiding catheter may also have the plurality of abutting portions located in a first portion of the guiding catheter, the abutting portions being spaced apart from the inner wall of the aorta when the guide wire is in the lumen in the first portion of the guiding catheter, and the method further including withdrawing the guide wire from the lumen in the portion of the guiding catheter, the withdrawing of the guide wire causing the abutting portions of the guiding catheter to abut the inner wall of the aorta at the two sites.

Another aspect of the disclosure here involves a guiding catheter configured to be inserted into a renal artery of a living body via an aorta, the guiding catheter including a catheter body comprising two abutting portions spaced apart from one another along a longitudinal extent, the catheter body being flexible, and the catheter body possessing a distal portion; and the two abutting portions configured to abut an inner wall of the aorta at two spaced apart sites when the distal portion of the catheter body is disposed in the renal artery of the living body, the two different sites of the inner wall being on an abdominal side below the heart, the two different sites being spaced apart and located diametrically opposite one another on the inner wall of the aorta, the two abutting portions being separated from one another by a non-abutting portion which does not abut the inner wall of the aorta when the two abutting portions abut the inner wall of the aorta. The guiding catheter may be configured so that each abutting portion of the catheter body includes a curved portion, and the non-abutting portion is a linear portion connecting the two curved portions.

DETAILED DESCRIPTION

Set forth below is a detailed description of embodiments of a guiding catheter for the renal artery and a method for using a guiding catheter representing examples of the inventive renal artery guiding catheter and method disclosed here.

Figure 1:
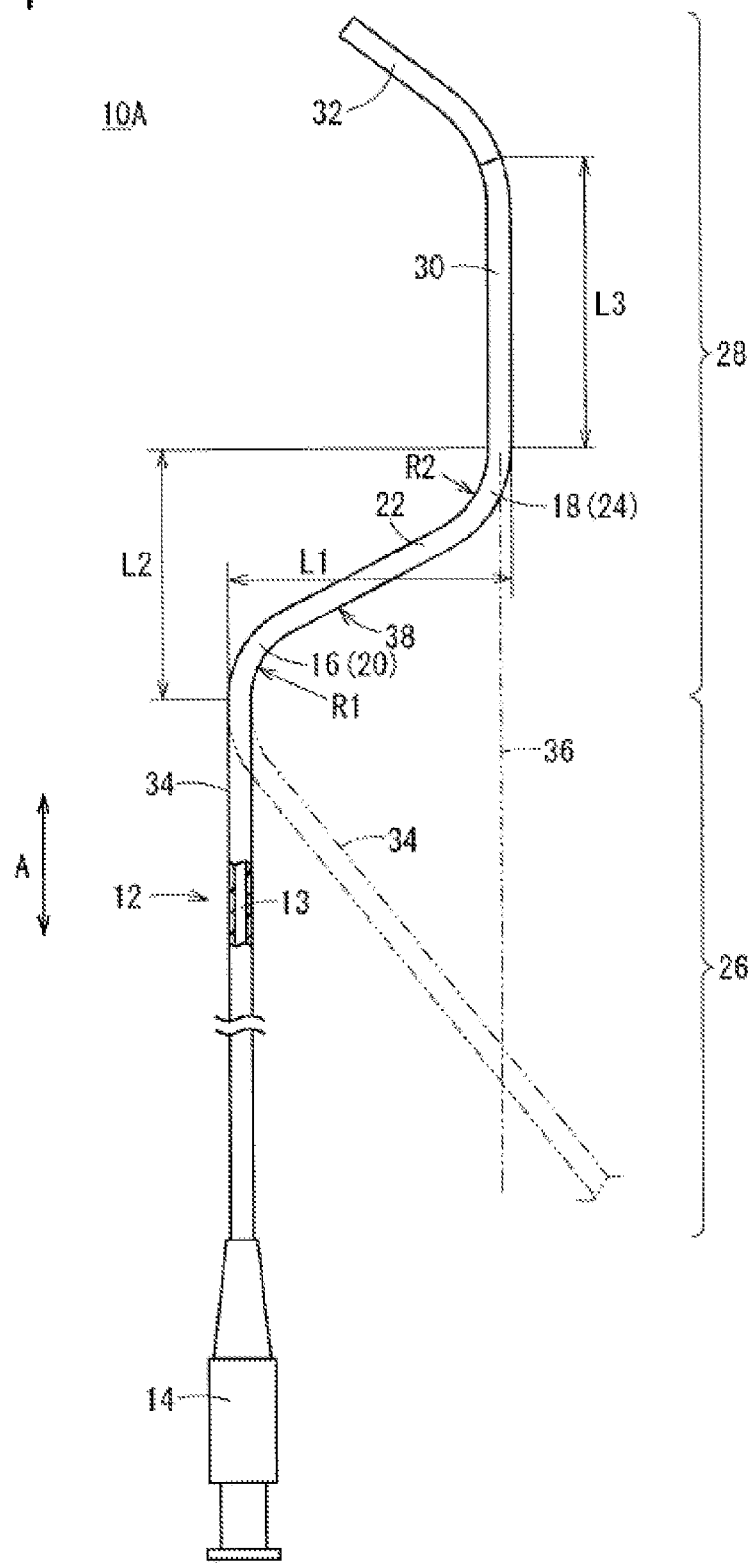
FIG. 1 is a partially omitted plan view showing a guiding catheter for the renal artery according to a first embodiment of the present invention.

FIG. 1 is a partially omitted plan view showing a configuration of a guiding catheter 10A for the renal artery (hereinafter, referred to as "guiding catheter 10A") according to a first embodiment. This guiding catheter 10A is configured to be inserted into a blood vessel of a patient from an artery in the arm (e.g., the brachial artery or the radial artery) to introduce a distal portion 32 of the guiding catheter 10A into the renal artery 50 (e.g., see FIG. 2) via the aorta 42. The guiding catheter 10A can reach the renal artery 50 after being extended from either an artery in the right arm or an artery in the left arm. The distal portion 32 of the guiding catheter 10A can be maneuvered to selectively engage openings (i.e., renal artery openings 51) of the right and left renal arteries 50.

As shown in FIG. 1, the guiding catheter 10A has a flexible catheter body 12 with a hollow structure and a hub 14 connected to a proximal portion of the catheter body 12.

The catheter body 12 has a lumen 13 which extends from a distal end to a proximal end of the catheter body 12. The outer diameter of the catheter body 12 is set to be less than or equal to 2.7 mm (preferably less than or equal to 2.1 mm) over the entire length of the catheter body 12 such that the guiding catheter 10A can be introduced from the brachial artery of a human and preferably from the radial artery of a human.

The catheter body 12 has a plurality of abutting portions 16 and 18 which can abut on at least two sites of the inner wall of the aorta 42 further on an abdominal side (tail side) than the heart 52 when the distal portion 32 is disposed in the target renal artery 50 (i.e., the two abutment sites are on the abdominal side of the heart, i.e., below the heart). The plurality of abutting portions 16 and 18 include a first curve 20 and a second curve 24 further on the distal portion 32 side than the first curve 20 (i.e., the second curve 24 is more distal than the first curve 20) that are connected through an intermediate portion 22 (i.e., a non-abutting portion) which extends from the distal end of the first curve 20.

In the embodiment illustrated in FIG. 1, the catheter body 12 has an elongated body portion 26 extending from the hub 14 and constituting most of the catheter body 12 (i.e., the elongated body portion 26 is longer than the other portions of the catheter body). The catheter body 12 also possesses a curved portion 28 extending from the body portion 26 up to the most distal end of the catheter body 12. The curved portion 28 possesses a curved shape in a free state (i.e., when no force is applied to the curved portion 28). The body portion 26 in the example shown in the drawing is substantially in a straight shape (i.e., it possesses a substantially straight shape) in a free state. The length of the body portion 26 is, for example, about 1000 mm to 1500 mm and preferably about 1000 mm to 1200 mm. The term "free state" means a state in which no force is applied to the body.

The curved portion 28 includes the first curve 20 which is curved and extends from the body portion 26, the intermediate portion 22 extending from the first curve 20, the second curve 24 which is curved and extends from the intermediate portion 22, an extension portion 30 extending from the second curve 24, and the distal portion 32 extending from the extension portion 30 to the distal most end of the catheter body 12. The entirety of the curved portion 28 illustrated in FIG. 1 exists within the same plane (i.e., the entirety of the curved portion 28 is coplanar), but the curved portion 28 is not limited to this configuration.

The first curve 20 and the second curve 24 are curved in directions opposite to each other (i.e., the first curve 20 possesses a curvature that is in the opposite direction of the curvature of the second curve). In the example shown in the FIG. 1, the distal portion 32 is curved in the same direction as the second curve 24. The first curve 20 possesses a curvature radius R1 and a curve angle in a free state of, for example, about 5 mm to 30 mm and about 45° C. to 90° C., respectively. The second curve 24 possesses a curvature radius R2 and a curve angle in a free state of, for example, about 5 mm to 30 mm and about 45° C. to 90° C., respectively. Note that the shape of each curvature of the first curve 20 and the second curve 24 may not be an accurate arc (i.e., may not possess a continuous radius of curvature).

The intermediate portion 22 extends in a substantially straight shape (e.g., the intermediate portion 22 of this embodiment may be a linear portion). An extension portion 34 (i.e., a first extension portion) extending from the first curve 20 in the proximal direction also possesses a substantially straight shape in a free state in the example shown in FIG. 1, but the extension portion 34 may also be curved. The extension portion 30 (i.e., a second extension portion) extending from the second curve 24 in the distal direction possesses a substantially straight shape in a free state in the example shown in FIG. 1, but the extension portion 30 may also be curved.

In the catheter body 12, a shaped portion 38 is formed by the first curve 20, the intermediate portion 22, and the second curve 24 (i.e., the shaped portion 38 includes the first curve 20, the intermediate portion 22, and the second curve 24). A first length L1 of the shaped portion 38 in a free state, in a direction orthogonal to a longitudinal direction (arrow "A" illustrates the longitudinal direction in FIG. 1) of the guiding catheter 10A is longer than the inner diameter of the aorta 42 (in which the shaped portion 38 is disposed) when the distal portion 32 is disposed in the renal artery 50. Accordingly, the first length L1 of the shaped portion 38 is set to, for example, about 12 mm to 40 mm, preferably about 14 mm to 30 mm, and more preferably about 15 mm to 26 mm. At such a first length L1, the first curve 20 and the second curve 24 can be made to abut two opposite sites of the inner wall of the aorta 42 when the distal portion 32 is disposed in the target renal artery 50 (i.e., the first curve 20 contacts one portion of the inner wall of the aorta 42 and the second curve 24 contacts an opposite portion of the inner wall of the aorta 42).

The second length L2 of the shaped portion 38 is in the longitudinal direction "A" of the guiding catheter 10A and is shorter than the first length L1. Therefore, when the distal portion 32 is in the target renal artery 50, the first curve 20 (which is proximal of the second curve 24) can be easily disposed at a position away from the heart 52.

In FIG. 1, the extension portion 34 (i.e., the first extension portion) on the proximal side of the shaped portion 38 and the extension portion 30 (i.e., the second extension portion) on the distal side of the shaped portion 38 extend almost in parallel with each other. However, the angle of curvature of the first curve 20 may be increased and the extension portion 34 may be instead positioned as shown by the virtual line in FIG. 1. In this configuration, an extension line 36 on the proximal side of the extension portion 30 (i.e., an imaginary or virtual line extending proximally from the extension portion 30) may intersect the extension portion 34 on the proximal side of the shaped portion 38.

The length L3 of the extension portion 30 extending from the second curve 24 and joining to the distal portion 32 may be longer than the length of the renal artery 50 of a human (i.e., the length from a renal artery opening 51 which is connected to the aorta 42 to the first bifurcated portion). For example, the length L3 of the extension portion 30 is about 20 mm to 120 mm, preferably about 30 mm to 100 mm, and more preferably about 40 mm to 60 mm. With such a length L3 of the extension portion 30, even in a case where the distal portion 32 of the catheter body 12 is put into a back side of the target renal artery 50, it is possible to maintain the first curve 20 and the second curve 24 in abutment with opposite sides of the inner wall of the aorta 42 without the second curve 24 entering the renal artery 50.

It is preferable that the distal portion 32 is more flexible than the section of the catheter body 12 proximal of the distal portion 32. The distal portion 32 is inserted into the renal artery 50. Therefore, the distal portion 32 of the curved portion 28 exhibits excellent flexibility making it less likely that the distal portion 32 will damage the inner walls of the renal artery 50. In the catheter body 12, the section proximal of the distal portion 32 may have enhanced flexibility toward the distal direction (i.e., the distal portion 32 is more flexible than the section immediately proximal of the distal portion 32, and the section immediately proximal of the distal portion 32 may be more flexible than other more proximal sections of the catheter body 12). With such a configuration, it is possible to improve blood vessel followability when the catheter passes through a blood vessel with a large curvature and to obtain favorable torque transmission performance.

The catheter body 12 may have an inner layer and an outer layer located outside of the inner layer. In this case, it is possible to constitute the inner layer using a synthetic resin with appropriate flexibility. Examples of the inner layer material include fluorine-containing resins such as PFA (copolymer of tetrafluoroethylene and perfluoroalkoxyethylene), PTFE (polytetrafluoroethylene) or the like. Examples of the outer layer material include polymeric materials such as polyolefins (for example, polyethylene, polypropylene, polybutene, an ethylene-propylene copolymer, an ethylene-vinyl acetate copolymer, an ionomer, a mixture of two or more thereof, or the like), polyvinyl chloride, polyamide, polyester, a polyester elastomer, a polyamide elastomer, polyurethane, a polyurethane elastomer, polyimide, a fluorine-containing resin and the like, or a mixture of more than one of these materials. A reinforcement layer may be provided between the inner layer and the outer layer. The reinforcement layer may be formed of a mesh-like blade in which thin wires (e.g., made of metal or resin) are interwoven.

The guiding catheter 10A is inserted into a blood vessel while an operator observes the position of the guiding catheter under radioscopy. For this reason, it is preferable to mix in a radiopaque material such as barium sulfate, bismuth oxide, or tungsten with the material constituting the catheter body 12.

The guiding catheter 10A according to the embodiment illustrated in FIG. 1 is constituted as described above. Next, the action and the effect of the guiding catheter will be described. The method for using the guiding catheter 10A is a manual operation aiming for a reduction in blood pressure by partially damaging sympathetic nerves around the renal artery 50. The terms "right", "right side", "left" and "left side" mean the right, right side, left and left side, respectively, from the patient's perspective.

In this manual operation, first, the guiding catheter 10A constituted as described above is provided (provision step). Next, the guiding catheter 10A is inserted from an artery in the arm and the distal portion 32 is disposed in the renal artery 50 via the aorta 42 (disposition step). In the disposition step, an artery in the arm of a patient is punctured with a catheter introducer (e.g., an introducer sheath, not shown on FIG. 1) before introducing the guiding catheter 10A into the artery (brachial artery or radial artery) in the arm of the patient.

Next, a guide wire 39 is inserted into the guiding catheter 10A (e.g., through the lumen 13 of the guiding catheter), and the guiding catheter 10A is inserted into the catheter introducer. The distal end of the catheter body 12 is then inserted into a blood vessel in a state in which the guide wire 39 precedes the distal end of the catheter body 12. That is, the distal end of the catheter body 12 is introduced into the blood vessel in a state in which the guide wire 39 is positioned in the catheter body 12 and the distal end of the guide wire 39 extends distally beyond the distal end of the catheter body 12.

Figure 2:
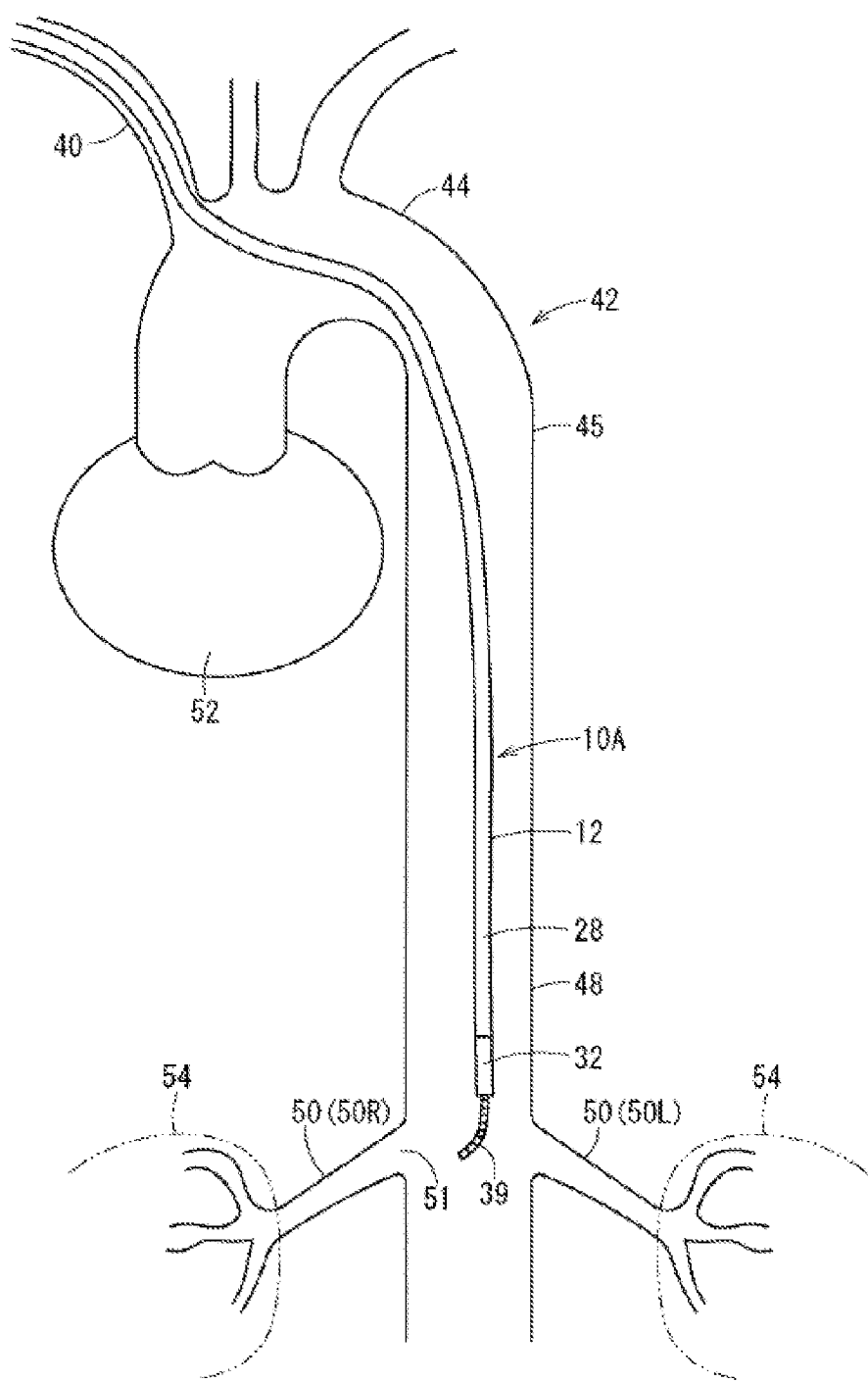
FIG. 2 is a first view illustrating a method for using the guiding catheter for the renal artery shown in FIG. 1.

Next, the guiding catheter 10A and the guide wire 39 are made to travel (i.e., are advanced or moved) within the blood vessel while forming a radioscopic image. The distal portion 32 of the guiding catheter 10A is advanced to reach the vicinity of the right and left renal arteries 50 (50R and 50L) connected to the right and left kidneys 54 from the brachiocephalic trunk 40 via the aortic arch 44 and the descending aorta 45 as shown in FIG. 2. When the distal end of the catheter body 12 passes through a bent section of the blood vessel, manual operations including taking in and out of the guide wire 39 and moving forward/backward and rotation of the guiding catheter 10A are appropriately carried out.

FIG. 2 illustrates that the curved portion 28 of the guiding catheter 10A is stretched by the guide wire 39, and therefore has a substantially straight shape (i.e., the guide wire 39 in the lumen 13 causes the curved portion 28 to maintain a more straightened shape as the guiding catheter 10A is advanced through the aorta 42).

Figure 3:
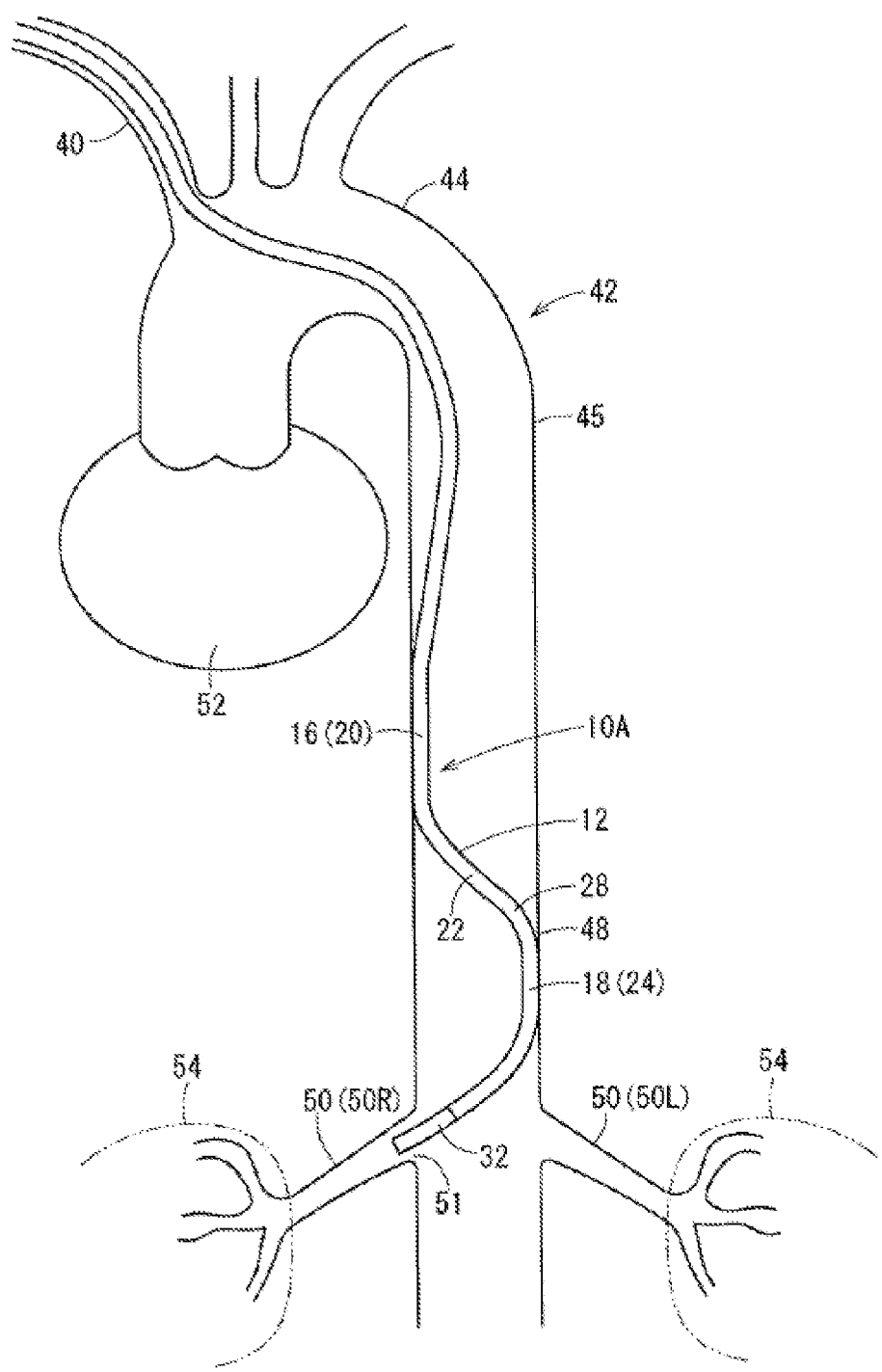
FIG. 3 is a second view illustrating a method for using the guiding catheter for the renal artery shown in FIG. 1.

Thereafter, when the guide wire 39 is pulled out of the catheter body 12, the curved portion 28 returns to its original curved shape shown in FIG. 1 (i.e., in the free state with no force applied, the curved portion 28 will take the curved shape). As shown in FIG. 3, the distal portion 32 of the catheter body 12 is positioned to face the renal artery opening 51 of the renal artery 50R on the right side and is inserted into the renal artery opening 51 due to repulsive force generated by the shape restoration. In other words, the curved body 28 returning to the curved shape causes the distal portion 32 of the catheter body 12 to be inserted into the renal artery opening 51. Accordingly, the distal portion 32 enters and engages with the opening 51 of the renal artery 50R. If the distal portion 32 is not automatically inserted into the renal artery 50R when the curved body 28 returns to the curved shape, the distal portion 32 may be relatively easily inserted into the renal artery 50R by the operator lightly rotating a hand-side portion of the guiding catheter 10A in an appropriate manner.

After the distal portion 32 is disposed in the target renal artery 50R or in parallel with the distal portion 32 being inserted into the target renal artery 50R, the abutting portions 16 and 18 (i.e., a plurality of abutting portions) move to abut portions of the inner wall of the aorta 42 at sections further on the abdominal side than the heart 52 (abutment step). In other words, the abutting portions 16 and 18 contact locations on the inner wall of the aorta that are on the abdominal side of the heart 52 (i.e., below the heart 52). When the first curve 20 and the second curve 24 are positioned in an abdominal aorta 48 and the guide wire 39 is removed from the guiding catheter 10A, the first curve 20 returns to its curved shape to abut an inner wall (e.g., the inner wall on the right side of the patient in the example shown in the FIG. 3) of the aorta 42 on the same side as the renal artery 50R that the distal portion 32 is inserted into, and the second curve 24 returns to its curved shape to abut the inner wall (e.g., the inner wall on the left side of the patient in the example shown in FIG. 3) of the aorta 42 on the side opposite to the renal artery 50R that the distal portion 32 is inserted into.

At this time, the first curve 20 and the second curve 24 of the guiding catheter 10A dig into portions of the inner wall of the abdominal aorta 48 which are opposite to each other (i.e., the first curve 20 and the second curve 24 firmly or strongly press against and deform diametrically opposite portions of the inner wall of the abdominal aorta 48) since the first length L1 in FIG. 1 is longer than the inner diameter of the abdominal aorta 48. The abutting portion 16 is formed by the distal side of the body portion 26, the first curve 20, and the proximal side of the intermediate portion 22 abutting the inner wall of the abdominal aorta 48 due to the first curve 20 of the guiding catheter 10A being pressed against the inner wall of the abdominal aorta 48. Similarly, the abutting portion 18 is formed by the distal side of the intermediate portion 22, the second curve 24, and the proximal side of the extension portion 30 abutting the inner wall of the abdominal aorta 48 due to the second curve 24 of the guiding catheter 10A being pressed against the inner wall of the abdominal aorta 48. Accordingly, the plurality of abutting portions 16 and 18 of the guiding catheter 10A are brought into surface contact with the inner wall of the abdominal aorta 48.

This configuration causes the first curve 20 and the second curve 24 to be backed up and supported (i.e., the curved shape can be retained). Since the catheter body 12 is shaped as described above, back-up force is generated. The curved portion 28 of the catheter body 12 is favorably fixed to the abdominal aorta 48 due to this back-up force, and therefore, the distal portion 32 is hardly deviated from the opening 51 of the renal artery 50R (i.e., the distal portion 32 maintains its position in the opening 51 of the renal artery 50R).

Although not shown in FIG. 3, when the distal portion 32 of the guiding catheter 10A is disposed in the target renal artery 50R, a part of the body portion 26 may abut an inner wall in the vicinity of the brachiocephalic trunk opening or an inner wall of the aortic arch 44. Accordingly, the catheter body 12 of the guiding catheter 10A is more favorably fixed to a blood vessel since other sections also abut the inner wall of the blood vessel in addition to the plurality of abutting portions 16 and 18. Even if the body portion 26 of the guiding catheter 10A abuts the inner wall of the aorta in the vicinity of the brachiocephalic trunk opening or the inner wall of the aortic arch 44 near the heart 52, pulsation caused by the heart 52 is suppressed from being transmitted to the distal portion 32 of the guiding catheter 10A since the above-described plurality of abutting portions 16 and 18 (i.e., the portions including the first curve 20 and the second curve 24 which are further on the distal side than the body portion 26 in the guiding catheter 10A) are brought into surface contact with the inner wall of the aorta on an abdominal side below the heart.

After the distal portion 32 is disposed in the renal artery 50R through the above-described operation, a contrast medium is injected through a Y-connector (not shown) mounted at a rear end of the hub 14. The injected contrast medium passes through the lumen 13 so as to be ejected to the inside of the renal artery 50R (i.e., the target site) through a distal opening of the lumen 13. Accordingly, it is possible to confirm the position the distal portion 32 relative to the renal artery 50R to confirm that the distal portion 32 is inserted in the renal artery 50R and to form an image of the renal artery 50R.

Figure 4:
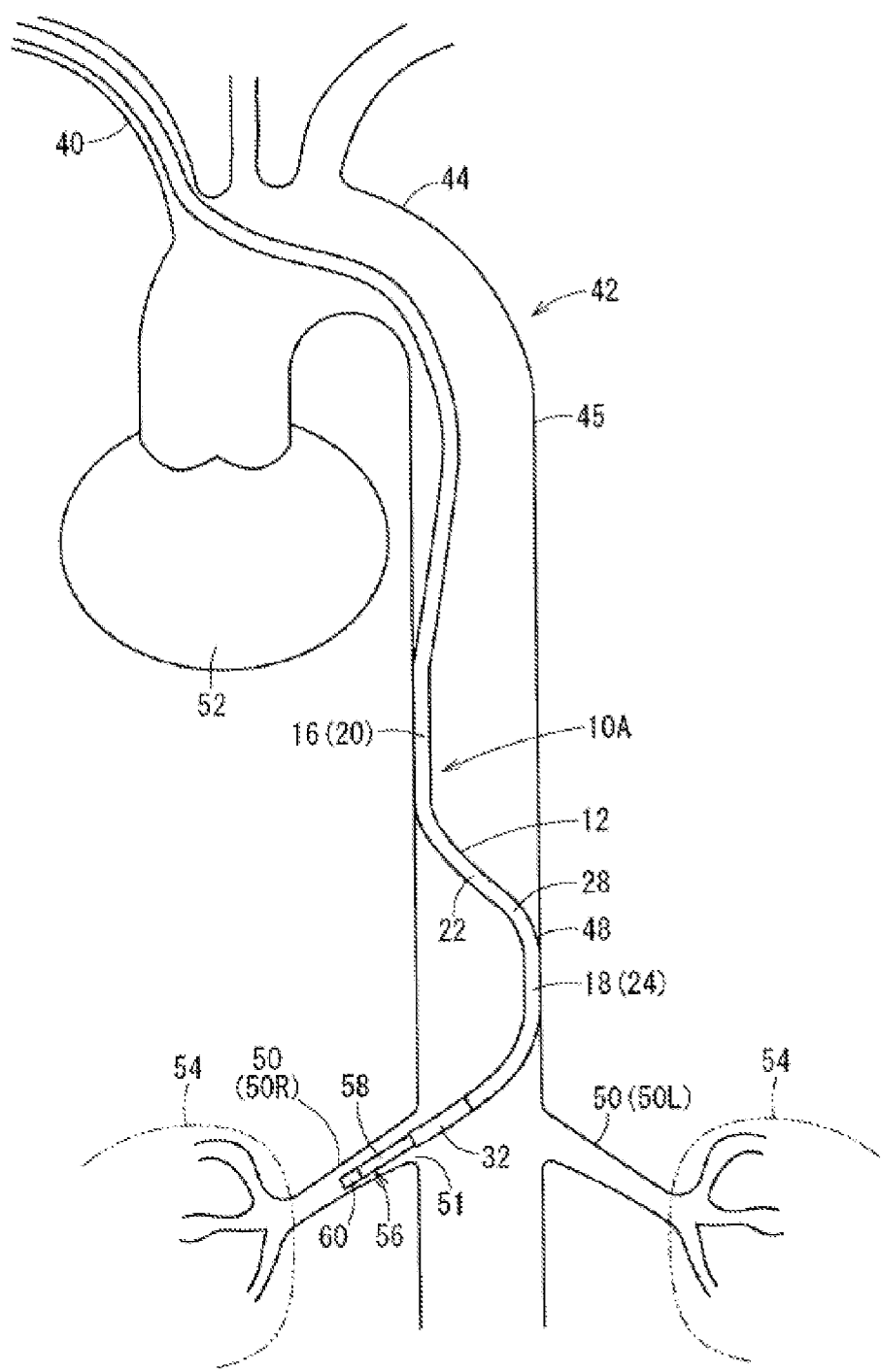
FIG. 4 is a third view illustrating a method for using the guiding catheter for the renal artery shown in FIG. 1.

Next, an ablation device 56 is inserted into the renal artery 50R via the rear end (i.e., proximal) portion of the Y-connector and the lumen 13 as shown in FIG. 4. This ablation device 56 has an elongated shaft 58 with flexibility, and an electrode portion 60 at a distal end of the shaft 58. The ablation device 56 is connected to a high frequency power source (not shown in FIG. 4) outside of the body, and is configured to apply a high frequency voltage to the electrode portion 60.

Sympathetic nerves around the renal artery 50R are cauterized (i.e., burned) in both the region that the electrode portion 60 contacts and the peripheral region near the region that the electrode portion 60 contacts. The electrode portion 60 cauterizes these regions by contacting the inner wall of the renal artery 50R and applying the energy generated by the high frequency voltage. The cauterized sympathetic nerves are damaged, and thus, the transmission function of the sympathetic nerves is interrupted. When cauterizing the sympathetic nerves using the electrode portion 60, a physiological salt solution may be injected through the Y-connector mounted at the rear end of the hub 14 of the guiding catheter 10A. to the physiological salt solution simply and easily reduces heat generated during the cauterizing in the region that the electrode portion 60 contacts and the peripheral region.

Treatment in which energy is applied to sympathetic nerves to cauterize and damage the sympathetic nerves is performed in a plurality of sites of the renal artery 50R. Thereafter, the ablation device 56 and the guiding catheter 10A are pulled out of the body from the blood vessel of the patient and treatment of closing the wound of the arm is carried out to complete the manual operation.

In sum, the guiding catheter 10A of this embodiment includes the plurality of abutting portions 16 and 18 (i.e., including the first curve 20 and the second curve 24) of the catheter body 12 that abut at least two sites of the inner wall of the aorta 42 on the abdominal side of the heart 52 when the distal portion 32 is in the target renal artery 50. These abutting portions 16, 18 make it possible to suppress a vibration of the catheter body 12 caused by the influence of the pulsation of the heart 52 or a pulsatile flow of blood from affecting the distal portion 32 of the catheter body 12. Accordingly, it is possible to suppress and stabilize the vibration of the electrode portion 60 when performing ablation treatment on biological tissue (e.g., sympathetic nerve) using the electrode portion 60 at the distal end by inserting the ablation device 56 into the guiding catheter 10A. The impedance during the application of energy is thus stabilized and the energy applied is maintained in the intended range. In addition, it is possible to provide desired application energy per unit area with respect to the inner surface of a blood vessel, and therefore, an intended effect is easily obtained.

In the embodiment illustrated in FIG. 1, the first curve 20 and the second curve 24 are in the abdominal aorta 48 in the state in which the distal portion 32 is disposed in the target renal artery 50. Accordingly, the first curve 20 and the second curve 24 abut on sites away from the heart 52, in the aorta 42 (i.e., the abutment sites are towards the abdomen and are below the heart). For this reason, the pulsation of the heart 52 is hardly transmitted to the catheter body 12, and the vibration of the catheter body 12 is suppressed.

The first curve 20 and the second curve 24 abutting opposite sites on the inner wall of the aorta 42 provides further stability to the catheter body 12. Therefore, it is possible to effectively suppress the vibration of the catheter body 12.

As described above, the first length L1 (as shown in FIG. 1) of the shaped portion 38 with respect to the direction orthogonal to the longitudinal direction (direction "A" in FIG. 1 is the longitudinal direction) of the guiding catheter 10A is longer than the inner diameter of the aorta 42 in which the shaped portion 38 is disposed when the distal portion 32 is disposed in the renal artery 50. For this reason, it is possible to make the first curve 20 and the second curve 24 reliably abut the inner wall of the aorta 42 at sites opposite to each other, and therefore, the catheter body 12 is stably fixed to the aorta 42.

The second length L2 (as shown in FIG. 1) of the shaped portion 38 is appropriately short so that it is possible to easily dispose the first curve 20 at a position away from the heart 52 when the distal portion 32 of the catheter body 12 is disposed in the renal artery 50. Since the first curve 20 is proximal of the second curve 24, both the first curve 20 and the second curve 24 are located at a position away from the heart 52. Accordingly, it is possible to effectively suppress the vibration of the catheter body 12.

As shown in the virtual line in FIG. 1, when the catheter body is configured such that the extension line 36 on the proximal side of the extension portion 30 intersects the extension portion 34, it is possible to make the length of the second curve 24 contacting an inner wall of the aorta 42 appropriately short, and therefore, it is possible to reduce the burden on the inner wall of the aorta 42.

When the length of the extension portion 30 is set to be longer than that of the renal artery 50, even when the distal portion 32 of the catheter body 12 is inserted into a back side (e.g., a side furthest away from the renal opening 51) of the renal artery 50, it is possible to favorably maintain the first curve 20 and the second curve 24 in abutment with the inner wall of the aorta 42 without the second curve 24 (i.e., the curve on the distal side) entering the renal artery 50.

Note that sympathetic nerves around the renal artery 50L on the left side may be damaged by disposing the distal portion 32 of the guiding catheter 10A in the renal artery 50L, inserting the ablation device 56 into the renal artery 50L on the left side through the guiding catheter 10A, and applying energy from the electrode portion 60. To operate on the renal artery 50L on the left side, the first curve 20 and the second curve 24 are positioned in the abdominal aorta 48 so that the first curve 20 abuts an inner wall on the left side of the aorta 42 (i.e., on the same side as that of the renal artery 50L into which the distal portion 32 is inserted), and the second curve 24 abuts an inner wall on the right side of the aorta 42 (i.e., on the side opposite to the renal artery 50L into which the distal portion 32 is inserted).

The above description discusses the manual operation of introducing the guiding catheter 10A from an artery in the right arm, but the guiding catheter 10A may instead be introduced from an artery in the left arm. Even when the guiding catheter 10A is introduced from the artery in the left arm, it is possible to dispose the distal portion 32 in either the right renal artery 50 or the left renal artery 50.

Figure 5:
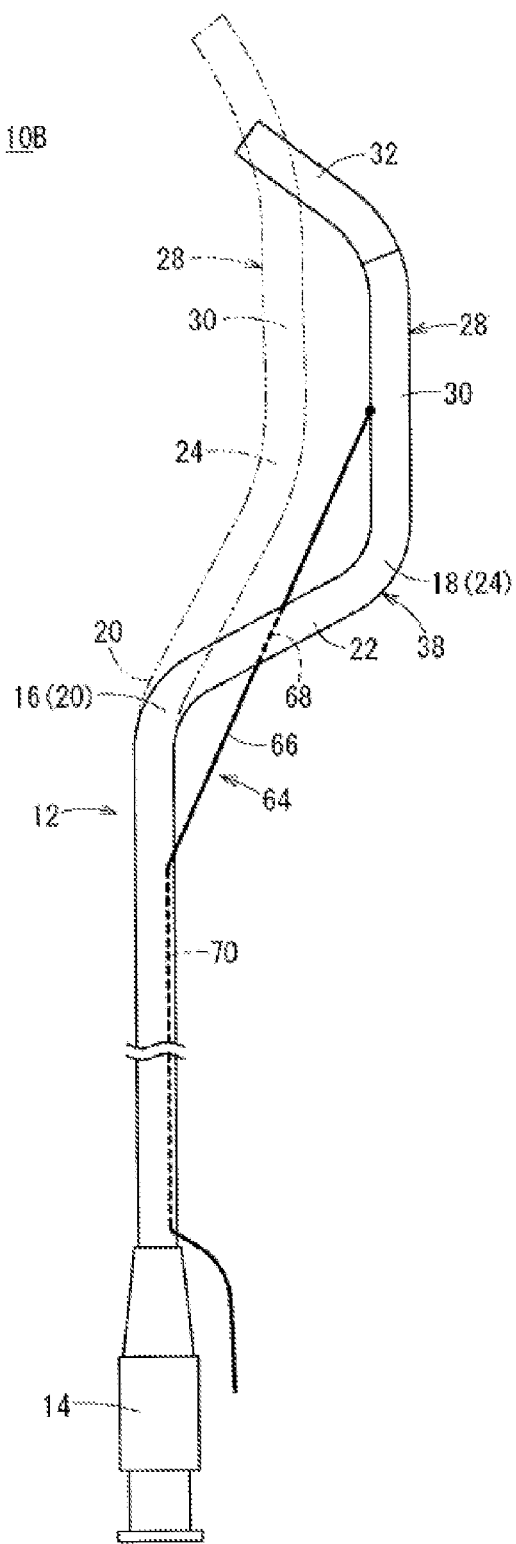
FIG. 5 is a partially omitted plan view showing a guiding catheter for the renal artery according to a second embodiment of the present invention.

FIG. 5 is a partially omitted plan view showing a guiding catheter 10B for the renal artery (hereinafter, called a "guiding catheter 10B") according to another embodiment of the present invention. Note that, in the guiding catheter 10B illustrated in FIG. 5, elements which exhibit the same or similar function and effect as those of the guiding catheter 10A according to the embodiment illustrated in FIG. 1 will be denoted by the same reference numerals, and the detailed description of these components will not be repeated.

The guiding catheter 10B illustrated in FIG. 5 is different from the guiding catheter 10A illustrated in FIG. 1 in that the guiding catheter 10B includes a shape control mechanism 64 and a structure relating to the shape control mechanism 64 is provided in the catheter body 12. This shape control mechanism 64 makes the first curve 20 and the second curve 24 enter a desired curved state.

The shape control mechanism 64 includes a traction wire 66. A distal end of the traction wire 66 is fixed further on the distal portion 32 side than the second curve 24 (i.e., the distal-most end of the traction wire 66 is located distally of the second curve 24), and the traction wire 66 extends more proximally than the first curve 20. The traction wire 66 is a linear member having flexibility (i.e., a flexible linear member), and can be formed of, for example, a metallic material, a resin material or the like.

Figure 6A:
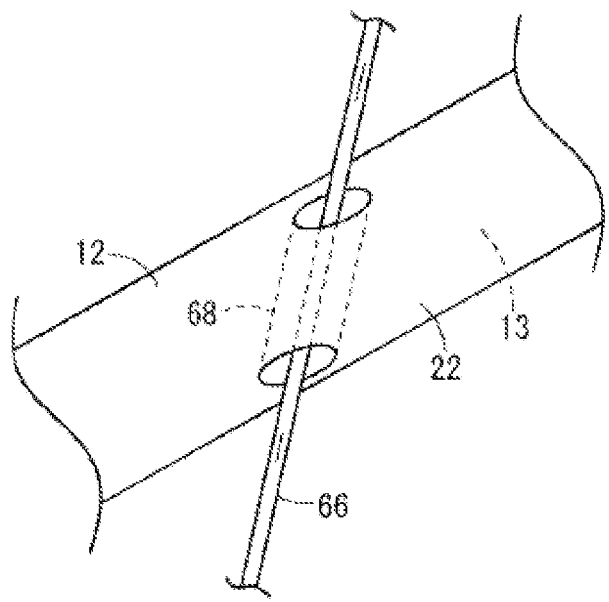
FIG. 6A is a view showing a guide portion in the guiding catheter for the renal artery shown in FIG. 5.

FIG. 5 illustrates that the distal end of the traction wire 66 is fixed to the extension portion 30 between the distal portion 32 and the second curve 24. As shown in FIG. 6A, a guide portion 68 is provided in the intermediate portion 22. The guide portion 68 allows a part of the traction wire 66 to be slidably inserted into and through the guide portion 68. The guide portion 68 can be positioned so that the halfway point of the traction wire 66 from the distal end of the lumen 70 to the fixed distal end of the traction wire 66 is within the guide portion 68. The guide portion 68 of the example shown in FIG. 6A is a hole. This hole is independent of the lumen 13 of the catheter body 12 and extends in a direction intersecting the lumen 13. The hole constituting the guide portion 68 may instead be oriented in parallel with the lumen 13.

Figure 6B:
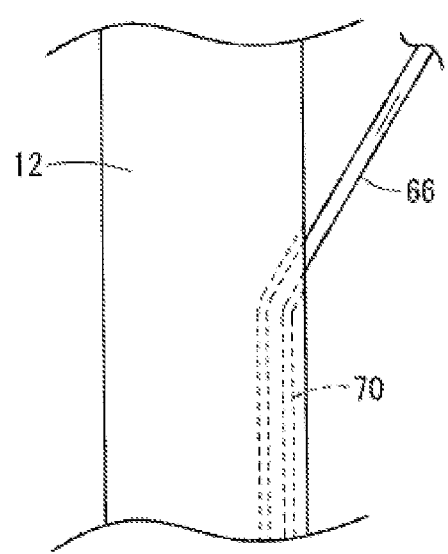
FIG. 6B is a view showing a lumen for a wire in the guiding catheter for the renal artery shown in FIG. 5.

As shown in FIGS. 5 and 6B, another part of the traction wire 66 is slidably inserted into a lumen 70 (i.e., the lumen 70 is configured to contain the traction wire 66) in a section further on the proximal side than the first curve 20 in the catheter body 12. The proximal side of the traction wire 66 is drawn from a proximal opening of the lumen 70 in the vicinity of the proximal end of the catheter body 12. Accordingly, an operator (i.e., a user) can move and operate the traction wire 66 in the proximal direction by grasping and pulling the proximal side of the traction wire 66 in a state in which the guiding catheter 10B is inserted into a blood vessel of a patient.

In the guiding catheter 10B provided with the shape control mechanism 64, each curvature of the first curve 20 and the second curve 24 becomes large in accordance with the movement of the traction wire 66 when the traction wire 66 is pulled in the proximal direction with respect to the catheter body 12. Accordingly, it is possible to make the first curve 20 and the second curve 24 enter a desired curved state by operating the shape control mechanism 64 even when the ablation device 56 is inserted into the guiding catheter 10B.

Since the ablation device 56 has rigidity (stiffness) to some extent, when the ablation device 56 is inserted into the guiding catheter 10B, the curved portion 28 may be extended to take the position shown by, for example, the virtual line in FIG. 5. In this case, the back-up support caused by the first curve 20 and the second curve 24 coming into contact with inner wall of the aorta 42 cannot be obtained. To overcome this problem, the extension portion 30 between the distal portion 32 and the second curve 24 is pulled in the proximal direction by an operator pulling the traction wire 66 proximally out of the body of a patient. Then, each curvature of the first curve 20 and the second curve 24 becomes larger, and the first curve 20 and the second curve 24 can be made into the desired curved shape. Accordingly, the first curve 20 and the second curve 24 can reliably abut the inner wall of the aorta 42.

Note that, in the embodiment illustrated in FIG. 5, the same or similar action and effect as those caused by each of the common constituent portions in the embodiment of FIG. 1 can be obtained.

Figure 7:
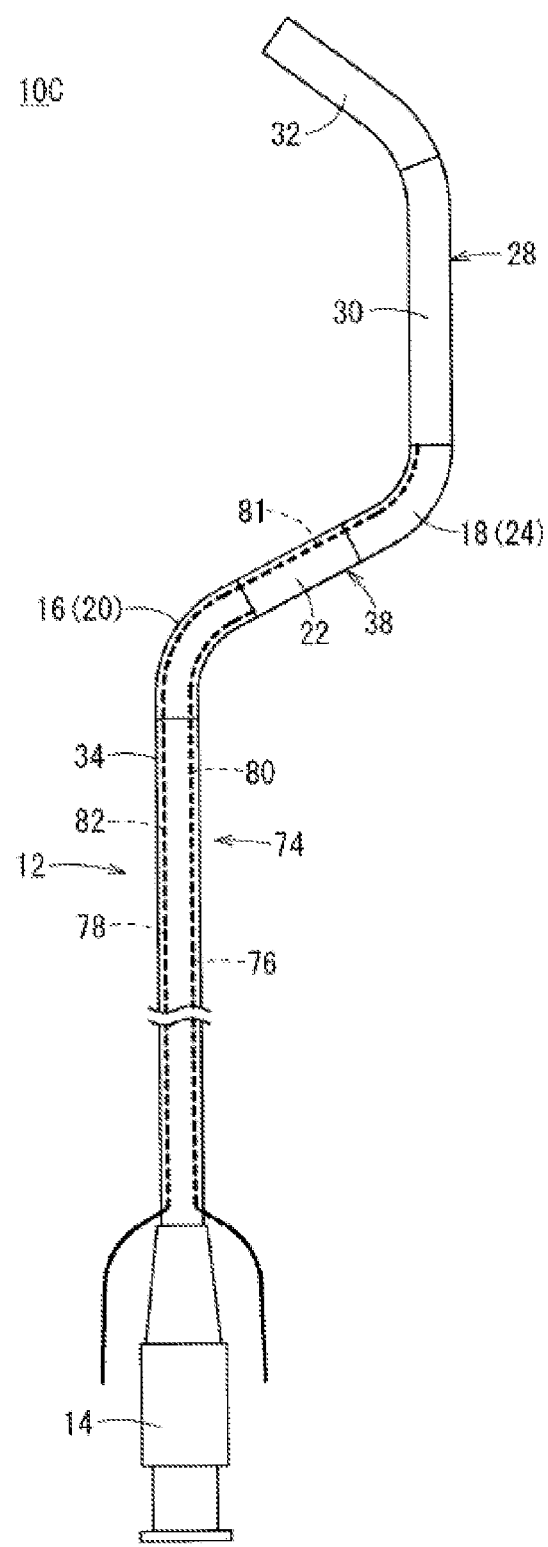
FIG. 7 is a partially omitted plan view showing a guiding catheter for the renal artery according to a third embodiment of the present invention.

FIG. 7 is a partially omitted plan view showing a guiding catheter 10C for the renal artery (hereinafter, called a "guiding catheter 10C") according to another embodiment. In the guiding catheter 10C according to the third embodiment, elements which exhibit the same or similar function and effect as those of the guiding catheter 10A according to the first embodiment will be denoted by the same reference numerals, and the detailed description of these components will not be repeated.

The guiding catheter 10C according to the embodiment illustrated in FIG. 7 is different from the guiding catheter 10A according to the embodiment illustrated in FIG. 1 in that the guiding catheter 10C includes a shape control mechanism 74 and a structure relating to the shape control mechanism 74 is provided in the catheter body 12. This shape control mechanism 74 is a mechanism for making the first curve 20 and the second curve 24 enter a desired curved state.

The shape control mechanism 74 includes a first traction wire 76 along the catheter body 12 that is used for operating the first curve 20, and a second traction wire 78 along the catheter body 12 that is used for operating the second curve 24. Each of the first traction wire 76 and the second traction wire 78 is a linear member having flexibility (i.e., a flexible linear member), and can be formed of, for example, metal, resin or the like.

The first traction wire 76 is connected to the first curve 20 and is slidably inserted into a lumen 80 (i.e., the lumen 80 is configured to contain the first traction wire 76) in a section further on the proximal side than the first curve 20. The proximal side of the first traction wire 76 is drawn from a proximal opening of the lumen 80 in the vicinity of the proximal end of the catheter body 12. Accordingly, an operator (user) can move and operate the first traction wire 76 in the proximal direction by grasping and pulling the proximal side of the first traction wire 76 when the guiding catheter 10C has been inserted into a blood vessel of a patient.

The second traction wire 78 is inserted into and connected to the second curve 24 and is slidably inserted into the intermediate portion 22, the first curve 20, and the catheter body 12 on the proximal side of the first curve 20. Lumens 81 and 82 are configured to contain the second traction wire 78, so that the second traction wire 78 is slidably insertable within the lumens 81, 82. The lumens 81, 82 extend in the catheter body 12 proximally of the intermediate portion 22 and the first curve 20.

The proximal side of the second traction wire 78 is drawn from a proximal opening of the lumen 82 for a second wire in the vicinity of the proximal end of the catheter body 12. Accordingly, an operator (user) can move and operate the second traction wire 78 in the proximal direction by grasping and pulling the proximal side of the second traction wire 78 when the guiding catheter 10C has been inserted into a blood vessel of a patient.

Figure 8A:
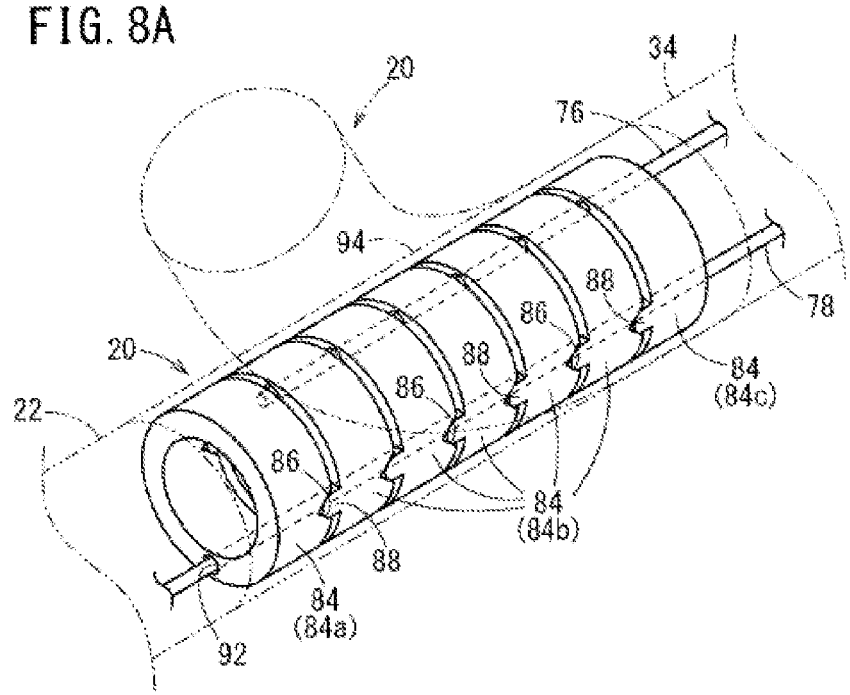
FIG. 8A is a perspective view showing a structure of a first curve in the guiding catheter for the renal artery shown in FIG. 7

The first curve 20 and the second curve 24 of the embodiment illustrated in FIG. 7 possess a structure in which they can change curvature. As shown in FIG. 8A, the first curve 20 has a plurality of first joint members 84 (i.e., including 84a to 84c) which are connected to each other in an axial direction. In FIG. 8A, the left side is a distal side and the right side is a proximal side. The plurality of first joint members 84 are connected to each other so as to be tiltable at a predetermined angle. Each of the first joint members 84 is formed in an annular shape. Each of the first joint members 84 can be formed of, for example, a metallic material, a resin material or the like.

The plurality of first joint members includes a first joint member 84a at the most distal side, at least one intermediate first joint member 84b, and a first joint member 84c at the most proximal side. Two V-shaped groove portions 86 are provided on a proximal surface of the first joint member 84a at the most distal side, at 180° intervals in the circumferential direction. Two protruding portions 88 with round distal ends are provided on a distal surface of the first joint member 84c at the most proximal side, at 180° intervals in the circumferential direction. Two protruding portions 88 are provided on a distal surface of each intermediate first joint member 84b at 180° intervals in the circumferential direction and two groove portions 86 are provided on a proximal surface of each intermediate first joint member 84b at 180° intervals in the circumferential direction. The adjacent first joint members 84 become tiltable by having the contact sites between each of the protruding portions 88 and each of the groove portions 86 as a supporting point by inserting each of the protruding portions 88 into each of the groove portions 86. Instead of the configuration of FIG. 8A, each of the protruding portions 88 may be provided on the proximal surface of each of the first joint members 84 and each of the groove portions 86 may be provided on the distal surface of each of the first joint members 84.

Figure 9:
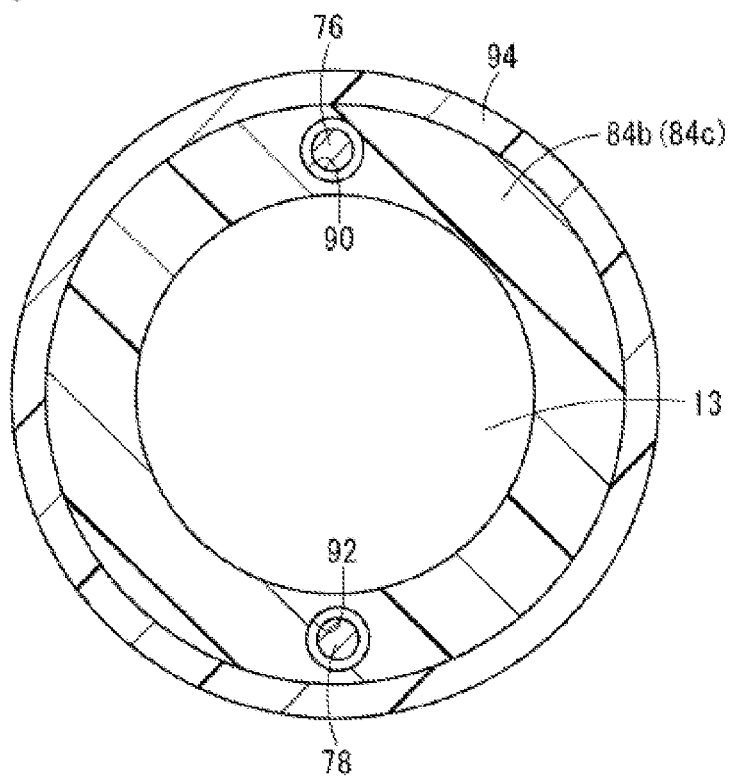
FIG. 9 is a cross-sectional view of a first joint member constituting the first curve in the guiding catheter for the renal artery shown in FIG. 7.

As shown in FIG. 9, a first guide hole 90 into which the first traction wire 76 is slidably inserted and a second guide hole 92 into which the second traction wire 78 is slidably inserted are provided in the intermediate first joint member 84b and the first joint member 84c on the most proximal side. The first guide hole 90 and the second guide hole 92 are provided on a side opposite to each other by having the center (axial line) of the first joint members 84 as a reference (i.e., the first guide hole 90 and the second guide hole 92 are diametrically opposite one another or are spaced 180° apart around the circumference of the lumen 13).

As shown in FIG. 8A, the second guide hole 92 is provided in the first joint member 84a on the most distal side. The second traction wire 78 extends beyond (i.e., more distally) the second guide hole 92 which is provided in the first joint member 84a on the most distal side and is connected to the second curve 24. The distal end of the first traction wire 76 is connected and fixed to the first joint member 84a on the most distal side. In the first curve 20, the outside of the plurality of first joint members 84 is covered by a flexible covering tube 94.

Figure 8B:
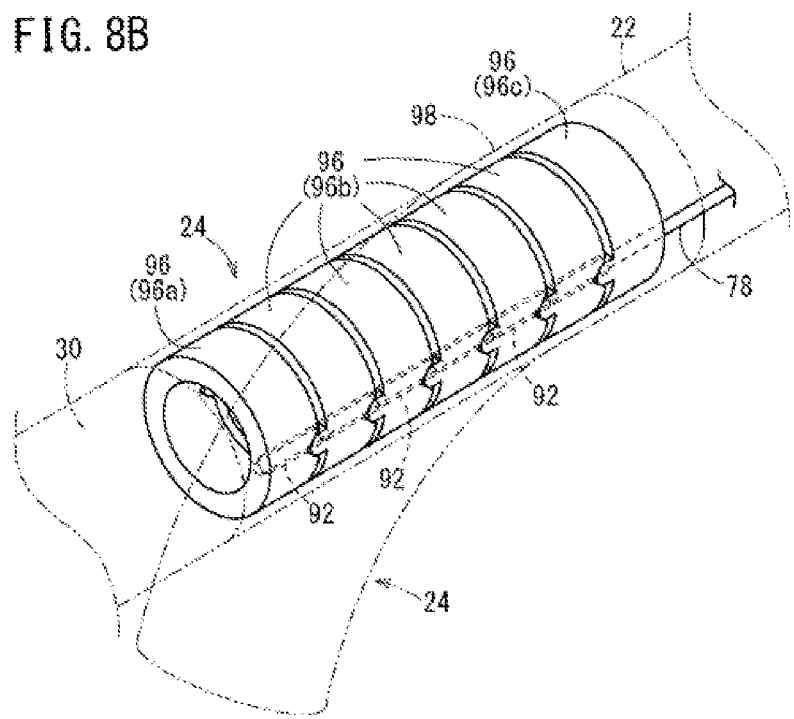
FIG. 8B is a perspective view showing a structure of a second curve in the guiding catheter for the renal artery shown in FIG. 7.

As shown in FIG. 8B, the second curve 24 includes a plurality of second joint members 96 (i.e., including 96a to 96c) which are connected to each other in an axial direction. Each of the second joint members 96 is formed in an annular shape. Each of the second joint members 96 can be formed of, for example, a metallic material, a resin material or the like. In the second curve 24, the second guide hole 92 is provided in each of an intermediate second joint member 96b and a second joint member 96c on the most proximal side, and the second traction wire 78 is inserted into these second guide holes 92. The distal end of the second traction wire 78 is connected and fixed to the second joint member 96a on the most distal side. In the second curve 24, the outside of the plurality of second joint members 96 is covered by a flexible covering tube 98.

In the guiding catheter 10C provided with the shape control mechanism 74 as described above, when the first traction wire 76 is pulled in the proximal direction, the curvature of the first curve 20 increases in accordance with the movement of the first traction wire 76 in the proximal direction of the catheter body 12, and the first curve 20 curves as illustrated, for example, by the virtual lines in FIG. 8A. In other words, when the first traction wire 76 is pulled by an operator in the proximal direction, the first joint member 84a on the most distal side is pulled by the first traction wire 76 in the proximal direction, and accordingly, the entire first curve 20 is curved.

When the second traction wire 78 of the guiding catheter 10C is pulled in the proximal direction, the curvature of the second curve 24 increases in accordance with the movement of the second traction wire 78 in the proximal direction of the catheter body 12, and the second curve 24 curves as illustrated, for example, by the virtual lines in FIG. 8B. In other words, when the second traction wire 78 is pulled by an operator in the proximal direction, the second joint member 96a on the most distal side is pulled by the second traction wire 78 in the proximal direction, and accordingly, the entire second curve 24 is curved.

According to the guiding catheter 10C of the embodiment illustrated in FIG. 7, it is possible to make the first curve 20 and the second curve 24 enter a desired curved state through the action of the shape control mechanism 74 even when the ablation device 56 is inserted into the guiding catheter 10C. That is, it is possible to make the first curve 20 and the second curve 24 have a desired curved shape by increasing the curvature of the first curve 20 and/or the second curve 24 through the operation of pulling the first traction wire 76 and the second traction wire 78 out of the body of a patient (i.e., increasing the curvature by pulling the first traction wire 76 and/or the second traction wire 78 in the proximal direction). Accordingly, the first curve 20 and the second curve 24 can reliably abut inner wall of the aorta 42.

In this embodiment, it is possible to individually (i.e., independently) control the curved state of each of the first curve 20 and the second curve 24 using the two traction wires 76 and 78.

Note that in the embodiment illustrated in FIG. 7, the same or similar action and effect as those caused by each of the common constituent portions in the embodiment of FIG. 1 can be obtained.

The detailed description above describes embodiments of a guiding catheter and a method for using the guiding catheter in a renal artery that represent examples of the inventive renal artery guiding catheter and method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A method for inserting a guiding catheter into a renal artery of a living body, the method comprising:
   inserting a guide wire into a blood vessel of the living body by way of a radial artery in an arm of the living body;
   inserting the guiding catheter into the blood vessel of the living body by way of the radial artery in the arm of the living body along the guide wire, the guiding catheter possessing an extension portion, a distal portion and a lumen, a proximal end of the distal portion being connected to a distal end of the extension portion, the guide wire being in the lumen of the guiding catheter while the guiding catheter is beign inserted into the living body, the living body having an aorta connected to a heart and a renal artery, the extension portion being linear and having a proximal end;
   moving the guiding catheter into and along the aorta using the guide wire in the lumen of the guiding catheter;
   withdrawing the guide wire proimally relative to the guiding catheter so that the guide wire is removed from the lumen of the guiding catheter and then from the living body, the withdrawing of the guide wire causing a plurality of abutting portions of the guiding catheter to abut two spaced apart sites of an inner wall of the aorta, the two spaced apart sites of the inner wall of the aorta being on an abdominal side below the heart in the aorta, the plurality of abutting portions being proximal to the proximal end of the extension portion of the guiding catheter, one of the plurality of abutting portions being contiguous with the proximal end of the extension portion; and
   the withdrawing of the guide wire causing the distal portion of the guiding catheter to extend distally into the renal artery, the distal end of the extension portion being above the renal artery within the living body when the distal portion of the guiding catheter extends into the renal artery and the distal portion of the guiding catheter extending linearly downwards from the distal end of the extension portion within the living body into the renal artery.

2. The method for using the guiding catheter according to claim 1, wherein the aorta is an abdominal aorta, and the two spaced apart sites are two spaced apart sites on the inner wall of the abdominal aorta.

3. The method for using the guiding catheter according to claim 1, wherein the plurality of abutting portions comprises a first curve and a second curve, a part of the first curve and a part of the second curve abutting the two spaced apart sites on the inner wall of the aorta on diametrically opposite sides of the aorta.

* * * * *